United States Patent

Inoue et al.

[11] 4,341,665
[45] Jul. 27, 1982

[54] ACYLNORBORNANONE ACETALS, PROCESS FOR PREPARING THE SAME, AND PERFUME COMPOSITIONS CONTAINING THE SAME

[75] Inventors: Yoshiharu Inoue, Ohsaka; Fumio Tanimoto, Kyoto; Hisao Kitano, Ohsaka, all of Japan

[73] Assignee: Nippon Petrochemicals Co., Ltd., Japan

[21] Appl. No.: 240,953

[22] Filed: Mar. 5, 1981

[30] Foreign Application Priority Data

Mar. 7, 1980 [JP] Japan ............... 55-29693
Mar. 7, 1980 [JP] Japan ............... 55-29694
Jun. 18, 1980 [JP] Japan ............... 55-82593

[51] Int. Cl.³ ............ C11B 9/00; C07D 319/04; C07D 317/72
[52] U.S. Cl. ............ 252/522 R; 549/336
[58] Field of Search ............ 260/340.9 R, 340.7; 252/522

[56] References Cited

U.S. PATENT DOCUMENTS 3,748,344  7/1973  McCloud et al. ............ 260/340.9 R
3,816,415  6/1974  Fauran et al. ............ 260/340.9 R
3,953,516  4/1976  Corbier et al. ............ 260/340.9 R Primary Examiner—Ethel G. Love Attorney, Agent, or Firm—Ostrolenk, Faber, Gerb & Soffen

[57] ABSTRACT

An acylnorbornanone acetal is represented by the formula:

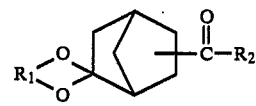

(wherein $R_1$ is a saturated hydrocarbon group having 2 to 7 carbon atoms and $R_2$ is a hydrogen atom or a hydrocabon group having 1 to 10 carbon atoms). The acylnorbornanone acetal is prepared by oxidizing an $\alpha$-hydroxyalkylnorbornanone acetal represented by the formula:

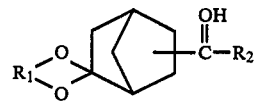

(wherein $R_2$ is a hydrogen atom or a hydrocarbon group having 2 to 7 carbon atoms). The perfume composition contains as a perfume component the acylnorbornanone acetal as represented above.

14 Claims, No Drawings

ACYLNORBORNANONE ACETALS, PROCESS FOR PREPARING THE SAME, AND PERFUME COMPOSITIONS CONTAINING THE SAME

BACKGROUND OF THE INVENTION

1. Field of the Invention

The present invention relates to novel derivatives of acylnorbornanone acetals, a process for preparing the same, and a perfume composition containing the same.

2. Description of the Prior Art

A variety of compounds having the norbornane ring has been heretofore prepared. For example, U.S. Pat. No. 3,860,635 discloses vinyl norbornanones, and U.S. Pat. No. 3,748,344 discloses cyclic acetals of norbornanone carboxaldehydes. However, no compounds are known in which the cyclic acetal moiety is linked through the spiro carbon atom with the norbornane ring. In addition, spiro cyclic type compounds are unknown which have an acyl group attached to the norbornane ring.

SUMMARY OF THE INVENTION

It has been found during the course of synthesis of compounds having the norbornane ring that a compound having an acyl group and a cyclic acetal linked through the spiro carbon atom with the norbornane ring has a woody fragrance and is useful as a component of perfume compositions. The present invention was completed on the basis of this finding.

Thus, the present invention includes acylnorbornanone acetals represented by the following general formula (I):

(wherein $R_1$ is a saturated hydrocarbon group having 2 to 7 carbon atoms and $R_2$ is a hydrogen atom or a hydrocarbon group having 1 to 10 carbon atoms); a process for preparing the same; and a perfume composition containing the same.

The compounds in accordance with the present invention may be prepared by the following reaction scheme;

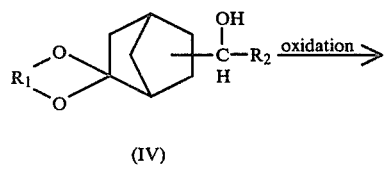

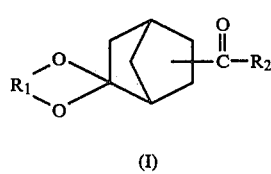

The oxidation should be conducted under a neutral or basic condition without causing the decomposition of the acetal linkage and collapsing the molecule in the oxidation.

DESCRIPTION OF THE PREFERRED EMBODIMENTS

The α-hydroxyalkylnorbornanone acetals represented by the above formula (IV) which can be used as raw materials in accordance with the present invention can be prepared by introducing the hydroxyl group into the α-position by means of a reaction such as hydroboration, oxymercuration, oxythallation or epoxidation of alkenylnorbornanone acetals represented by the following general formula (V):

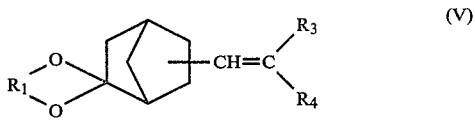

(wherein $R_1$ is a saturated hydrocarbon group having 2 to 7 carbon atoms, and $R_3$ and $R_4$ are independently a hydrogen atom or a hydrocarbon group such that the total number of carbon atoms when taken together is between 1 and 9) or alkylidenenorbornanone acetals represented by the following general formula (VI):

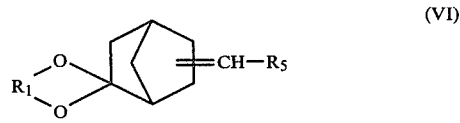

(wherein $R_5$ is a hydrogen atom or a hydrocarbon group having 1 to 10 carbon atoms, and $R_1$ has the same meaning as above).

Thus, the methods of introducing the hydroxyl group into the α-position of the compound represented by formula (V) or (VI) involve the addition to the unsaturated bond of the compound represented by either of the formulas, reduction and then hydrolysis. The methods may include:

(1) a method via oxymercuration which involves the reaction of a mercuric salt such as mercuric acetate with the compound of formula (V) to thereby add the mercuric salt to the unsaturated bond followed by demercuration and hydrolysis;

(2) a method via oxythallation which involves the same reaction as represented hereinabove using a thallium salt such as thallium nitrate;

(3) a method via hydroboration which involves the addition of a borane or the like to the unsaturated bond of the compound as represented by formula (IV) followed by oxidation and hydrolysis; and (4) a method via epoxidation which involves the addition of oxygen to the unsaturated bond by use of a peracid, a peroxide or molecular oxygen in the presence of a catalyst, reduction of the resultant epoxide, and hydrolysis.

These methods allow selective introduction of the hydroxyl group into the α-position of the double bond in a high yield and minimize side reactions such as isomerization. The methods also cause little decomposition of the acetal moiety of the raw material, norbornanone acetals, because all of the methods are carried out under non-acidic conditions.

In the method via oxymercuration represented as (1) above, the addition of a mercuric salt such as mercuric acetate, mercuric trifluoroacetate or mercuric nitrate to the alkenylnorbornanone acetal is carried out in a solvent such as water or a mixture thereof with tetrahydrofuran, acetonitrile, ethyl ether, methanol or ethanol at a temperature in the range of 5° to 130° C., preferably 15° to 80° C. The reaction is usually conducted under ambient pressure, but it may be conducted under a slightly reduced or elevated pressure. The amount of the mercuric salt to be used may be in the range of 0.5 to 2.0 moles with respect to one mole of an olefin to be added.

Then, the reductive elimination of mercury and the concurrent hydrolysis are conducted using sodium boron hydride, sodium hydroxide or sodium-liquid ammonia, thereby giving the α-hydroxyalkylnorbornanone acetal represented by formula (IV). The reaction is carried out at a temperature in the range of 0° to 50° C., preferably 0° to 30° C. The reaction pressure is usually ambient pressure, although it may be slightly reduced or elevated.

The method via oxythallation represented as (2) above can be carried out in the same manner as in the method via oxymercuration as set forth hereinabove, with the exception that a thallium salt such as thallium acetate, thallium trifluoroacetate or thallium nitrate is used in place of the mercuric salt.

In the method via hydroboration represented as (3) above, diborane or a substituted boron compound such as disiamylborane, dicyclohexylborane, thexylborane, diisopinocampheylborane, 9-borabicyclo[3.3.1]nonane, dichloroborane or the like is first added to the alkenyl- or alkylidenenorbornane acetal. The amount of the borane compound to be used may range from 0.1 to 1.0 mole for the diborane and from 0.5 to 2.0 moles for the substituted borane compound with respect to one mole of the olefin. As a solvent, an ether may be employed such as tetrahydrofuran, ethyl ether, dimethylcarbitol, diethylcarbitol or the like. The reaction temperature may range from −15° to 230° C., preferably from −5° to 60° C., and the reaction is usually conducted under ambient pressure, although the pressure may be slightly reduced or elevated. Then, the oxidative hydrolysis is effected in an aqueous solution or a solution of dimethylcarbitol, diethylcarbitol, tetrahydrofuran or ethyl alcohol containing a hydrogen peroxide-sodium hydroxide or an organic peracid-sodium hydroxide. The temperature for this reaction may range from 0° to 80° C., preferably from 5° to 50° C.

In the method via epoxidation represented as (4) above, the alkenyl- or alkylidene-norbornanone acetal epoxide is first produced by using a peracid or the like, separated by means of distillation or the like, and then reduced. The resulting product is then hydrolyzed.

In the reaction of producing the epoxide, there may be employed as a solvent a halogenated hydrocarbon such as chloroform, methylene chloride, carbon tetrachloride or the like; an aromatic hydrocarbon such as benzene, toluene, xylene or the like; an aliphatic hydrocarbon such as hexane, pentane, heptane or the like; an alicyclic hydrocarbon such as cyclopentane, cyclohexane or the like; an ester such as ethyl acetate, ethyl propionate or the like; or an ether such as ethyl ether, tetrahydrofuran or the like. In these solvents, the epoxide can be provided by means of an organic peracid such as peracetic acid, trifluoroperacetic acid, perbenzoic acid, performic acid, m-chloroperbenzoic acid, permaleic acid, perphthalic acid, perlauric acid or the like; an organic peroxide and the oxide of a transition metal such as molybdenum, vanadium or the like; hydrogen peroxide and an organic nitrile or oxygen in the presence of a catalyst of metals of the silver series, thallium series or palladium series. In the vapor phase reaction where the silver series, thallium series or palladium series metal catalyst is used, the reaction system may be diluted with an inert gas such as nitrogen gas or the like. The amount of the organic peracid or the like may range from 0.5 to 2.0 moles with respect to one mole of the olefin. The reaction may be carried out at a temperature in the range of −15° to 100° C., preferably −5° to 70° C., and under ambient pressure or under a slightly reduced or elevated pressure.

The epoxides prepared as hereinabove are then separated by means of distillation, extraction or the like and subjected to reduction and then hydrolysis. The reduction is effected in an ether such as ethyl ether, tetrahydrofuran, dimethylcarbitol, diethylcarbitol or the like; an aromatic hydrocarbon such as benzene, toluene, xylene or the like; or an aliphatic hydrocarbon such as hexane, pentane or the like; and with a variety of metal hydrides such as lithium aluminum hydride, lithium borohydride, sodium borohydride, aluminum hydride, dichloro-aluminum hydride, diisobutyl-aluminum hydride, diborane, cyanosodium borohydride, triethoxylithium aluminum hydride, tri-tertiary-butoxy-aluminum hydride, sodium aluminum hydride, disiamylborane or the like. The reduction is carried out at a temperature in the range of −80° to 100° C., preferably −70° to 50° C. After reduction, the hydrolysis is effected with methanol, ethanol, isopropanol, water or the like to provide the α-hydroxylalkylnorbornanone acetal.

For example, a vinylnorbornanone acetal as the alkenylnorbornanone acetal of formula (V) or a ethylidenenorbornanone acetal as the alkylidenenorbornanone acetal of formula (VI) can be produced from a Diels-Alder adduct between cyclopentadiene and butadiene according to the following reaction scheme:

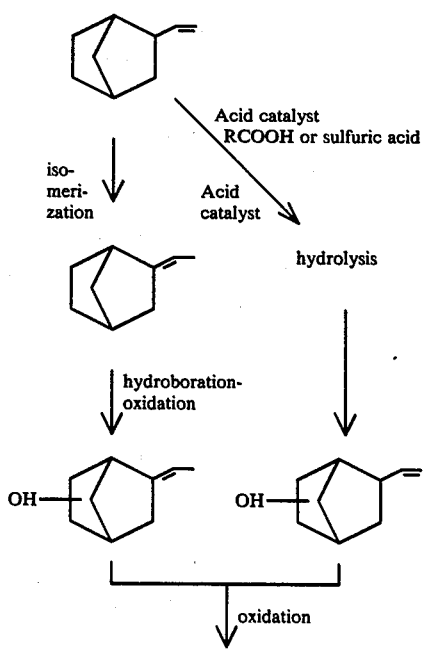

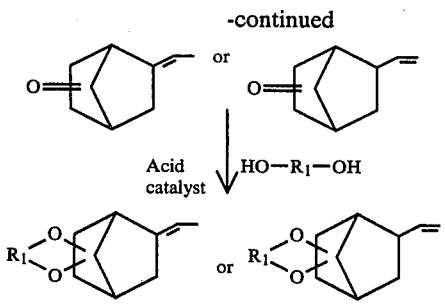

In the above scheme, RCOOH may include, for example, formic acid, acetic acid, propionic acid and the like, and the OH-R$_1$-OH to be employed for the last-mentioned acetals may include, for example, 1,2-diol or 1,3-diol.

The term "1,2-diol" referred to herein means a compound in which two hydroxyl groups are attached respectively to two adjacent carbon atoms of a saturated hydrocarbon. The term "1,3-diol" referred to herein means a compound in which two hydroxyl groups are attached respectively to two carbon atoms of a saturated hydrocarbon, with another carbon atom interposed between the said two carbon atoms.

Representatives of the 1,2-diols stated hereinabove may be ethylene glycol, 1,2-propanediol, 1,2-butanediol, 1,2-, 2,3- or 3,4-hexanediol, 1,2- or 2,3-pentanediol, 1,2-cyclohexanediol, methylcyclohexane-1,2-diol and the like.

Illustrative of the 1,3-diols may be 1,3-propane diol, 1,3-butanediol, 2,2-dimethyl-1,3-propanediol, 2,2-diethyl-1,3-propanediol, 2-methyl-1,3-propanediol, 2-ethyl-1,3-propanediol, 1,3-cyclohexanediol, methylcyclohexane-1,3-diol and the like.

In the reaction in which the corresponding acetals are formed, the diols represented hereinabove may be used singly or in a mixture thereof.

Where the acetals are produced with a 1,2-diol, a 1,3-dioxolane ring is formed, and where the acetals are prepared with a 1,3-diol, a 1,3-dioxane ring is formed.

The compounds represented by formula (V) or (VI) obtainable from the 5-vinyl- or ethylidene-2-norbornene as the aforesaid alkenyl- or alkylidene-norbornene in the manner as represented hereinabove may be, for example, spiro[1,3-dioxolane-2,2'- or 2,3'-(5'-vinyl- or ethylidene-norbornane)], spiro[4,5-dimethyl-1,3-dioxolane-2,2'- or 2,3'-(5'-vinyl- or ethylidene-nobornane)], spiro[1,3-dioxane-2,2'- or 2,3'-(5'-vinyl- or ethylidene-norbornane)], spiro[5,5'-dimethyl-1,3-dioxane-2,2'- or 2,3'-(5'-vinyl- or ethylidene-norbornane)], spiro[4-methyl-1,3-dioxane-2,2'- or 2,3'-(5'-vinyl- or ethylidene-norbornane)], spiro[5,5-diethyl-1,3-dioxane-2,2'- or 2,3'-(5'-vinyl- or ethylidene-norbornane)], spiro[4,5-tetramethylene-1,3-dioxolane-2,2'- or 2,3'-(5'-vinyl- or ethylidene-norbornane)] and the like.

The oxidation of the α-hydroxyalkylnorbornanone acetals then provides the corresponding acylnorbornanone acetals.

The oxidation to be practiced in the present invention should be effected under a neutral or basic condition without decomposing the acetal linkage and causing the cleavage of the molecule by the oxidation.

Accordingly, the oxidation method to be employed herein may be a method of oxidation with a ketone such as acetone, methyl ethyl ketone or quinone in the presence of an aluminum alkoxide such as aluminum triisopropoxide or the like (Oppenauer oxidation); a method of oxidation using, for example, pyridine-chromic anhydride complex; a method of oxidation with a chromate, a dichromate, a permanganate or the like; a method of oxidation with molecular oxygen in the presence of a copper series catalyst; a method of oxidation with a peroxide in a neutral or basic medium; or the like.

Among the methods of oxidation represented hereinabove, the Oppenauer oxidation employs an alkali metal alkoxide such as aluminum triisopropoxide, aluminum tri-tertiary-butoxide, aluminum triphenoxide or the like in an amount of 0.25 to 3 moles with respect to one mole of the alcohol in the presence of a large excess of an oxidizing agent such as a ketone, e.g., acetone, cyclohexanone, methyl ethyl ketone, benzophenone, parabenzoquinone or the like. The solvent to be employed may be, for example, an aromatic hydrocarbon such as benzene, toluene or xylene. The reaction may be carried out at a temperature in the range of 0° to 200° C., preferably 30° to 150° C., for 10 minutes to 68 hours, usually 15 minutes to 24 hours. In the reaction represented hereinabove, the oxidizing agent such as the ketone, e.g., acetone, is converted to an alcohol such as isopropylalcohol. Accordingly, the oxidation is accomplished in a better yield when it is carried out while distilling off the alcohol formed.

Where pyridine-chromic anhydride complex is used for the oxidation, pyridine or a chlorinated hydrocarbon such as methylene chloride, chloroform, carbon tetrachloride, ethylene dichloride or the like may be employed as a solvent. The oxidation may be carried out at a temperature ranging from 0° to 80° C., preferably 5° to 50° C., under ambient pressure or a slightly reduced or elevated pressure.

A method of oxidation with chromic acid which does not exert any influence on the acetal linkage can be carried out in a solvent such as acetic anhydride, acetic acid whose acidity is weakened with an alkali acetate, a benzene-acetic acid mixture, or a weakly basic solvent such as dimethylformamide or the like.

Vapor phase or liquid phase oxidation can be effected with molecular oxygen in the presence of the copper series catalyst. In the vapor phase oxidation, an inert gas such as nitrogen gas may be employed as a diluent.

In any case, any arbitrary solvent may be chosen for the oxidation reaction as long as it does not affect the oxidation reaction.

After the oxidation is conducted in the manner as set forth hereinabove, the solvent is distilled off to leave a residual material which is purified in the usual way to give the acylnorbornanone acetals.

The α-hydroxyalkylnorbornanone acetals in accordance with the present invention as represented by formula (IV) above have two structural isomers represented by the following formula (IVa) or (IVb):

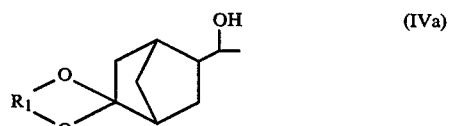 (IVa)

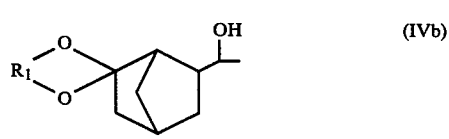 (IVb)

The acylnorbornanone acetals represented by formula (I) above also have two structural isomers as represented respectively by formulas (II) and (III) corresponding to formulas (IVa) and (IVb):

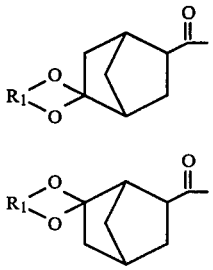

In these formulas, the symbol $R_1$ is a saturated hydrocarbon group having 2 to 7 carbon atoms.

The compounds to be represented by the above formula are, for example, spiro[1,3-dioxolane-2,2'- or 2,3'-(5'-acetyl-norbornane)], spiro[4,5-dimethyl-1,3-dioxolane-2,2'- or 2,3'-(5'-acetyl-norbornane)], spiro[1,3-dioxane-2,2'- or 2,3'-(5-acetyl-norbornane)], spiro[5,5'-dimethyl-1,3-dioxane-2,2'- or 2,3'-(5'-acetyl-norbornane)], spiro[4-methyl-1,3-dioxane-2,2'- or 2,3'-(5'-acetyl-norbornane)], spiro[5,5-diethyl-1,3-dioxane-2,2'- or 2,3'-(5'-acetyl-norbornane)] and spiro[4,5-tetramethylene-1,3-dioxolane-2,2'- or 2,3'-(5'-acetyl-norbornane)].

The compounds represented by formula (I) above which are the compounds in accordance with the present invention have stereoisomers, the endo- and exo-forms, corresponding to each of the structural isomers represented hereinabove. They may be represented for the 5-acetyl-2-norbornanone ethylene acetal or spiro[1,3-dioxolane-2,2'-(5'-acetyl-norbornane)] as follows:

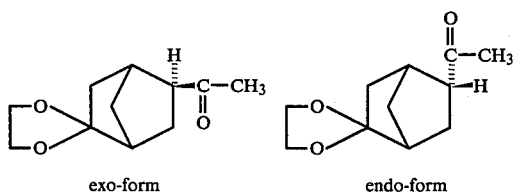

exo-form            endo-form

In accordance with the present invention, any of these stereoisomers are effective for perfume compositions. Accordingly, the compounds obtainable in the manner as set forth hereinabove may be employed in a mixture of stereoisomers as fragrance components, or they may naturally be employed as single compounds.

The compounds represented by formula (I) above are in a colorless, transparent liquid form, favorable in compatibility in any arbitrary amount with a solvent to be usually employed for a perfume, and mix with other solid perfume materials well.

These compounds are stable against oxidation and the like and do not undergo any transformations during storage for a long period of time. They cause no irritation upon contact with the skin and are nontoxic in use.

As they have the properties as stated hereinabove, the compounds as represented by formula (I) above in accordance with the present invention can be employed as compound perfumes useful for general fragrant cosmetics such as soaps, detergents, creams, toilet water and the like, and as fragrance materials for other daily commodities.

The acylonorbornanone acetals represented by formula (I) in accordance with the present invention may be synthesized, in addition to the methods as hereinabove stated, by the methods such as:

(A) a method utilizing the Diels-Alder reaction;
(B) a method utilizing the Friedel-Crafts reaction; and
(C) a method employing a dialkylcadmium, a lithium-dialkylcuprate.

The method (A) is a method involving the addition of an acylethylene such as methyl vinyl ketone to cyclopentadiene by means of the Diels-Alder reaction to give the acylnorbornene; the addition thereto of an acid; hydrolysis; oxidation; and acetalization.

The method (B) is one which involves the addition of an acyl halide to a 5-norbornene-2- or 3-one by means of the Friedel-Crafts reaction using a catalyst such as aluminum chloride, and the conversion of the resultant acylnorbornanone to the corresponding acetal.

The method (C) is a method involving the addition of an organic acid or sulfuric acid to a halogeno-norbornene such as 5-chloro-2-norbornene; hydrolysis; oxidation to give the norbornanone halide which in turn is converted into the norbornanone acetal halide; treatment of the acetal halide with a cadmium halide to give the dialkylcadmium or with an alkyl lithium and a copper halide to give the lithium dialkyl cuprate where the alkyl group mentioned above indicates substituted norbornyl group; and then reaction with an acyl halide.

In order to further explain the technical content of the present invention, it is illustrated by way of a preparation example and working examples as reference examples. The present invention should not be construed to be restricted to the working examples which follow, because they are chosen from many working examples. The present invention can be practiced by varying its working embodiments in an arbitrary manner as long as they do not deviate from the spirit and scope of the present invention.

The following illustrates examples for preparing the compounds represented by the formulas above and embodiments of the present invention by way of the working examples.

Preparation Example

Synthesis of spiro[1,3-dioxolane-2,2'- or 2,3'-(5'-α-hydroxyethyl-nornornane)]

Spiro[1,3-dioxolane-2,2'- or 2,3'-(5'-α-hydroxyethyl-norbornane)] was prepared from spiro[1,3-dioxolane-2,2'- or 2,3'-(5'-vinyl-norbornane)] by means of oxymercuration.

For this process, 12.0 g (0.067 mole) of spiro[1,3-dioxolane-2,2'- or 2,3'-(5'-vinyl-norbornane)] was dropwise added at room temperature to a mixture of 21.2 g (0.067 mole) of mercuric acetate, 60 ml of water and 60 ml of tetrahydrofuran. After the dropwise addition was completed, the mixture was stirred for about 10 minutes to give a colorless, clear solution to which was added 65 ml of an aqueous solution containing 8.2 g of sodium hydroxide, and then 65 ml of an aqueous solution of 1.4 g of sodium borohydride and 8.2 g of sodium hydroxide was added. After the mixture was stirred for 1 hour at room temperature, mercury was removed from the reaction mixture and sodium chloride was added thereto to a level of saturation. The resulting solution was extracted three times with a benzene-ether mixture, and the resulting organic layer was washed with a small amount of a sodium chloride saturated aqueous solution to remove the alkali material and dried over anhydrous magnesium sulfate. After the solvent was distilled off, the residual material was distilled under reduced pressure to leave 10.5 g of a colorless viscous liquid (yield, 79.1%; boiling point 104°–105° C./0.25 mmHg; $n_D^{22} = 1.4970$).

ir (neat method): ~3,500 cm$^{-1}$ (stretching vibration of O-H); the stretching vibration of the vinyl group C=C at 1,630 cm$^{-1}$ disappeared.

nmr (CDCl$_3$): 6.1 τ (singlet, 4H), 6.2–6.4 τ (multiplet, 1H), 7.6 τ (broad singlet), 7.3–8.9 τ (multiplet, 12H).

| Elemental analysis (as C$_{11}$H$_{19}$O$_3$): | | |
|---|---|---|
| | C % | H % |
| Calculated: | 66.3 | 9.5 |
| Found: | 66.5 | 9.6 |

EXAMPLE 1

Synthesis of spiro[1,3- dioxolane-2,2'- or 2,3'-(5'-acyl-norbornane)]

13.3 g (0.067 mole) of spiro[1,3-dioxolane-2,2'- or 2,3'-(5'-α-hydroxyethyl-norbornane)] was dissolved in 250 ml of dry toluene. To this mixture was added 100 ml of freshly distilled cyclohexanone, and 100 ml of a toluene solution of 7.2 g (0.036 mole) of aluminum triisopropoxide was dropwise added thereto. After the dropwise addition was completed, the reaction mixture was heated under reflux for 2 hours and then cooled to room temperature. Then, the mixture was poured into 100 ml of a sodium potassium tartrate saturated aqueous solution. After the organic layer was separated, the aqueous layer was extracted with a benzene-ether mixture. The extract was then combined with the organic layer previously separated and dried over anhydrous magnesium sulfate. The solvent was distilled off, and the residual material was distilled under reduced pressure to give the title colorless liquid (12.7 g; yield, 96.7%; boiling point 86° C./0.30 mmHg) having a floral woody fragrance.

ir (neat method): ~1,710 cm$^{-1}$ (stretching vibration of C=O). The stretching vibration of O-H at ~3,500 cm$^{-1}$ disappeared.

nmr (CDCl$_3$): 6.1 τ (singlet, 4H), 7.9 τ (singlet, 3H), 7.4–8.8 τ (multiplet, 9H).

| Elemental analysis (as C$_{11}$H$_{17}$O$_3$): | | |
|---|---|---|
| | C % | H % |
| Calculated: | 67.3 | 8.2 |
| Found: | 67.6 | 8.3 |

Gas chromatography (filler, Silicone SE-30; column material, stainless steel; column size, 0.25 cm (diameter×90 m; column temperature, 150° C.) revealed that spiro[1,3-dioxolane-2,2'-(5'-acetyl-norbornane)] amounted to 70% of the total, with the remainder being spiro[1,3-dioxolane-2,3'-(5'-acetyl-norbornane)], and that the ratio of the endo-form to the exo-form was about 30:70.

It was also observed that, in Examples 2 to 4 which follow, gas chromatography revealed substantially the same ratio in the corresponding structural isomers and stereoisomers as in Example 1.

EXAMPLE 2

Synthesis of spiro[4,5-dimethyl-1,3-dioxolane-2,2'- or 2,3'-(5'-acetyl-norbornane)]

Spiro[4,5-dimethyl-1,3-dioxolane-2,2'- or 2,3'-(5'-α-hydroxyethyl-norbornane)] was reacted in the same manner as in Example 1 to give the title spiro[4,5-dimethyl-1,3-dioxolane-2,2'- or 2,3'-(5'-acetyl-norbornane)].

Yield: 94.5%

Boiling point: 102° C./0.8 mmHg ir (neat method): ~1,710 cm$^{-1}$ (stretching vibration of C=O); the stretching vibration of O-H at ~3,500 cm$^{-1}$ disappeared.

nmr (CDCl$_3$): 6.0–6.2 τ (quartet, 2H), 7.9 τ (singlet, 3H), 7.0–8.7 τ (multiplet, 9H), 8.8–9.0 τ (triplet, 6H).

| Elemental analysis (as C$_{13}$H$_{20}$O$_3$): | | |
|---|---|---|
| | C % | H % |
| Calculated: | 69.6 | 8.9 |
| Found: | 69.3 | 8.7 |

EXAMPLE 3

Synthesis of spiro[1,3-dioxane-2,2'- or 2,3'-(5'-acetyl-norbornane)]

Spiro[1,3-dioxane-2,2'- or 2,3'-(5'-α-hydroxyethyl-norbornane)] was reacted in the same manner as in Example 1 to give the title spiro[1,3-dioxane-2,2'- or 2,3'-(5'-acetyl-norbornane)].

Yield: 95.0%

Boiling point: 107° C./0.2 mmHg ir (neat method): ~1,715 cm$^{-1}$ (stretching vibration of C=O); the stretching vibration of O-H at ~3,500 cm$^{-1}$ disappeared.

nmr (CDCl$_3$): 6.1–6.3 τ (triplet, 4H), 7.9 τ (singlet, 3H), 7.0–8.8 τ (multiplet, 11H).

| Elemental analysis (as C$_{12}$H$_{18}$O$_3$): | | |
|---|---|---|
| | C % | H % |
| Calculated: | 68.5 | 8.6 |
| Found: | 68.7 | 8.2 |

EXAMPLE 4

Synthesis of spiro[5,5-dimethyl-1,3-dioxane-2,2'- or 2,3'-(5'-acetyl-norbornane)]

Spiro[5,5-dimethyl-1,3-dioxane-2,2'- or 2,3'-(5'-α-hydroxylethyl-norbornane)] was reacted in the same manner as in Example 1 to given the title spiro[5,5-dimethyl-1,3-dioxane-2,2'- or 2,3'-(5'-acetyl-norbornane)].

Yield: 96.5%

Boiling point: 93° C./0.2 mmHg ir (neat method): ~1,715 cm$^{-1}$ (stretching vibration of C=O); the stretching vibration of O-H at ~3,500 cm$^{-1}$ disappeared.

nmr (CDCl$_3$): 6.1 τ (singlet, 4H), 7.9 τ (singlet, 3H), 7.2–8.8 τ (multiplet, 9H), 9.1 τ (singlet, 6H).

| Elemental analysis (as C$_{14}$H$_{22}$O$_3$): | | |
|---|---|---|
| | C % | H % |
| Calculated: | 70.6 | 9.3 |

| Elemental analysis (as $C_{14}H_{22}O_3$): | | |
|---|---|---|
| | C % | H % |
| Found: | 70.1 | 9.5 |

EXAMPLE 5

The spiro[1,3-dioxolane-2,2'- or 2,3'-(5'-acetylnorbornane)] prepared in Example 1 was formulated in the following composition. The formulation was suitable for a perfume base for men in fougere note.

| | |
|---|---|
| Oakmoss Oil, (Texas) | 2 g |
| Bergamot Oil, (Bourbon) | 10 g |
| Lavender Oil, (England) | 13 g |
| Rhodinol | 10 g |
| β-Phenylethyl alcohol | 6 g |
| Patchouli Oil (Ceylon) | 3 g |
| Geranium Oil, (France) | 4 g |
| Methylionone | 12 g |
| Cyclopentadecanolide | 1 g |
| Petitgrain Oil, (Paraguay) | 5 g |
| Coumarin | 10 g |
| Musk ketone | 6 g |
| Heliotropine | 6 g |
| Phenylethyl salicylate | 3 g |
| Jasmone | 3 g |
| Benzyl salicylate | 3 g |
| Acetal prepared in Example 1 | 3 g |
| Total | 100 g |

EXAMPLE 6

The spiro[4,5-dimethyl-1,3-dioxolane-2,2'- or 2,3'-(5'-acetyl-norbornane)] prepared in Example 2 was formulated into the following composition to provide a perfume composition in muguet note having the fragrance of lily of the valley. This composition was suitable for perfumes in soaps and toiletries.

| | |
|---|---|
| Citronellol | 24 g |
| Rhodinol | 10 g |
| β-phenylethyl alcohol | 25 g |
| Hydroxycitronellal | 13 g |
| Benzyl acetate | 6 g |
| Jasmone | 4 g |
| α-Amylcinnamic aldehyde | 4 g |
| 10% Indole.ethanoic solution | 2 g |
| Linalool | 5 g |
| Cyclopentadecanolide | 1 g |
| 10% ethylvanillin.ethanolic solution | 1 g |
| Acetal prepared in Example 2 | 5 g |
| Total | 100 g |

EXAMPLE 7

The spiro[1,3-dioxane-2,2'- or 2,3'-[5'-acetylnorbornane)] prepared in Example 3 was formulated into the following composition to provide a perfume composition of cypress base in floral bouquet note. The composition was suitable for hair oil, hair spray, hand creams and the like.

| | |
|---|---|
| Oakmoss Oil, (French) | 5 g |
| Patchouli Oil, (Bourbon) | 3 g |
| Vetiver Oil, (Bourbon) | 6 g |
| Sandal Wood Oil, (Mysore) | 5 g |
| Bergamot Oil, (Madagascar) | 17 g |
| Methylionone | 6 g |
| Linalool | 5 g |
| Jasmone | 2 g |
| Methyldihydrojasmonate | 2 g |
| Rose Absolute, (Burgalia) | 4 g |
| 10% Vanillin ethanolic solution | 3 g |
| Heliotropine | 3 g |
| Isoamyl salicylate | 2 g |
| Lily aldehyde | 5 g |
| Labdonum Oil, (Lebanon) | 3 g |
| β-Phenylpropyl alcohol | 5 g |
| Coumarin | 5 g |
| 10% indole.ethanolic solution | 5 g |
| Benzyl acetate | 9 g |
| Acetal prepared in Example 3 | 5 g |
| Total | |

EXAMPLE 8

The spiro[5,5-dimethyl-1,3-dioxane-2,2'- or 2,3'-(5'-acetyl-norbornane)] was formulated into the composition to provide a citrus fragrance in combination with bergamot aroma. This formulation was suitable for a perfume base in toilet water, eau de Cologne and soaps.

| | |
|---|---|
| Orange Oil, (Japan) | 7 g |
| Bergamot Oil, (Zanzibal) | 25 g |
| Lemon Oil, (California) | 5 g |
| Linalyl acetate | 6 g |
| Sandal Wood Oil, (Mysore) | 7 g |
| Patchouli Oil, (Bourbon) | 8 g |
| Lavender Oil, (England) | 5 g |
| β-Phenylethyl alcohol | 4 g |
| Methyldihydrojasmonate | 2 g |
| 10% indole.ethanolic solution | 0.5 g |
| Benzoin | 3 g |
| 0.3% Tongkining Musk Tincture | 2 g |
| 2% vanillin.ethanolic solution | 5 g |
| Coumarin | 8 g |
| 10% ethylene brassylate.ethanolic solution | 3 g |
| Linalool | 4 g |
| Methyl anthranilate | 0.5 g |
| Dimethylbenzylcarbinyl acetate | 1 g |
| Acetal prepared in Example 4 | 4 g |
| Total | 100 g |

What is claimed is:

1. An acylnorbornanone acetal represented by the following formula (I):

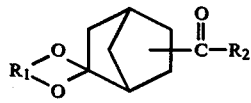

(I)

(wherein $R_1$ is a saturated hydrocarbon group having 2 to 7 carbon atoms and $R_2$ is a hydrogen atom or a hydrocarbon group having 1 to 10 carbon atoms).

2. An acylnorbornanone acetal according to claim 1, wherein the said acylnorbornanone acetal is represented by the following formula (II) or (III):

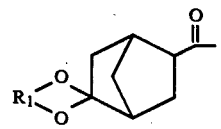

(II)

-continued

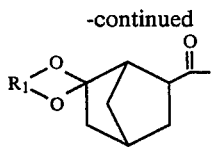
(III)

(wherein $R_1$ is a saturated hydrocarbon group having 2 to 7 carbon atoms).

3. An acylnorbornanone acetal according to claim 1 wherein $R_1$ is a saturated hydrocarbon group having 2 to 7 carbon atoms and completes the formation of a 1,3-dioxolane or 1,3-dioxane ring.

4. An acylnorbornanone acetal according to claim 2, wherein the compound represented by formula (II) or (III) is spiro[1,3-dioxolane-2,2'- or 2,3'-(5'-acetylnorbornane)].

5. An acylnorbornanone acetal according to claim 2, wherein the compound represented by formula (II) or (III) is spiro[4,5-dimethyl-1,3-dioxolane-2,2'- or 2,3'-(5'-acetyl-norbornane)].

6. An acylnorbornanone acetal according to claim 2, wherein the compound represented by formula (II) or (III) is spiro[1,3-dioxane-2,2'- or 2,3'-(5'-acetylnorbornane)].

7. An acylnorbornanone acetal according to claim 2, wherein the compound represented by formula (II) or (III) is spiro(5,5-dimethyl-1,3-dioxane-2,2'- or 2,3'-(5'-acetyl-norbornane)].

8. A perfume composition characterized by containing a fragrance-effective amount of an acylnorbornanone acetal represented by formula (I):

(I)

(wherein $R_1$ is a saturated hydrocarbon group having 2 to 7 carbon atoms and $R_2$ is a hydrogen atom or a hydrocarbon group having 1 to 10 carbon atoms) and a suitable perfume adjuvant.

9. A perfume composition according to claim 8, wherein the acylnorbornanone acetal is represented by formula (II) or (III):

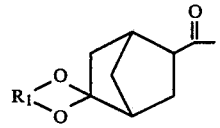
(II)

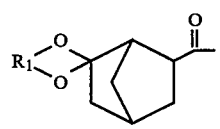
(III)

(wherein $R_1$ is a saturated hydrocarbon group having 2 to 7 carbon atoms).

10. A perfume composition according to claim 9 wherein $R_1$ is a saturated hydrocarbon group having 2 to 7 carbon atoms and completes the formation of a 1,3-dioxolane or 1,3-dioxane ring.

11. A perfume composition according to claim 9, wherein the compound represented by formula (II) or (III) is spiro[1,3-dioxolane-2,2'- or 2,3'-(5'-acetylnorbornane)].

12. A perfume composition according to claim 9, wherein the compound represented by formula (II) or (III) is spiro[4,5-dimethyl-1,3-dioxolane-2,2'- or 2,3-(5'-acetyl-norbornane)].

13. A perfume composition according to claim 9, wherein the compound represented by formula (II) or (III) is spiro[1,3-dioxane-2,2'- or 2,3'-(5'-acetylnorbornane)].

14. A perfume composition according to claim 9, wherein the compound represented by formula (II) or (III) is spiro[5,5-dimethyl-1,3-dioxane-2,2'- or 2,3'-(5'-acetyl-norbornane)].

* * * * *